United States Patent
Bhattacharjee et al.

(10) Patent No.: US 11,045,136 B2
(45) Date of Patent: Jun. 29, 2021

(54) HEART RATE DRIVEN UNSUPERVISED TECHNIQUES FOR CONTINUOUS MONITORING OF AROUSAL TREND OF USERS

(71) Applicant: Tata Consultancy Services Limited, Mumbai (IN)

(72) Inventors: Tanuka Bhattacharjee, Kolkata (IN); Shreyasi Datta, Kolkata (IN); Deepan Das, Kolkata (IN); Anirban Dutta Choudhury, Kolkata (IN); Arpan Pal, Kolkata (IN); Prasanta Kumar Ghosh, Bengaluru (IN)

(73) Assignee: Tata Consultancy Services Limited, Mumbai (IN)

( * ) Notice: Subject to any disclaimer, the term of this patent is extended or adjusted under 35 U.S.C. 154(b) by 120 days.

(21) Appl. No.: 16/190,800

(22) Filed: Nov. 14, 2018

(65) Prior Publication Data
US 2020/0000360 A1     Jan. 2, 2020

(30) Foreign Application Priority Data
Jun. 29, 2018 (IN) .............................. 201821024337

(51) Int. Cl.
| | |
|---|---|
| *A61B 5/04* | (2006.01) |
| *A61B 5/352* | (2021.01) |
| *G16H 40/63* | (2018.01) |
| *A61B 5/024* | (2006.01) |
| *A61B 5/16* | (2006.01) |
| *A61B 5/316* | (2021.01) |

(52) U.S. Cl.
CPC .......... *A61B 5/352* (2021.01); *A61B 5/02405* (2013.01); *A61B 5/165* (2013.01); *A61B 5/316* (2021.01); *G16H 40/63* (2018.01)

(58) Field of Classification Search
USPC .................................................. 600/519–520
See application file for complete search history.

(56) References Cited

U.S. PATENT DOCUMENTS

| | | | |
|---|---|---|---|
| 9,844,332 B2 | 12/2017 | Kushki et al. | |
| 2014/0275854 A1* | 9/2014 | Venkatraman ......... | A61B 5/681 600/301 |
| 2015/0080756 A1 | 3/2015 | Robinson et al. | |

FOREIGN PATENT DOCUMENTS

WO    WO-2008/065724      6/2008

* cited by examiner

*Primary Examiner* — Nicole F Lavert
(74) *Attorney, Agent, or Firm* — Finnegan, Henderson, Farabow, Garrett & Dunner LLP

(57) ABSTRACT

Traditionally arousal classification has been broadly done in multiple classes but have been insufficient to provide information about how arousal level of user changes over time. Present disclosure propose a continuous and unsupervised approach of monitoring the arousal trend of individual from his/her heart rate by obtaining instantaneous HR for time windows from a resampled time series of RR intervals obtained from ECG signal. A measured average heart rate (a measured $\overline{HR}$) is computed from instantaneous HR specific to user for each time window thereby estimating apriori state based on a last instance of an aposteriori state initialized and observation of a state space model of Kalman Filter is determined for computing error and normalizing thereof which gets compared with a threshold for continuous monitoring of arousal trend of the user. The aposterior state is further updated using Kalman gain computed based on measurement noise determined for state space model.

15 Claims, 8 Drawing Sheets

(a) $\delta = 0.14\ [0.09\ 0.23]$ (b) $\delta = 0.08\ [0.02\ 0.19]$

HEART RATE DRIVEN UNSUPERVISED TECHNIQUES FOR CONTINUOUS MONITORING OF AROUSAL TREND OF USERS

PRIORITY CLAIM

This U.S. patent application claims priority under 35 U.S.C. § 119 to: India Application No. 201821024337, filed on Jun. 29, 2018. The entire contents of the aforementioned application are incorporated herein by reference.

TECHNICAL FIELD

The disclosure herein generally relates to emotional state detection, and, more particularly, to heart rate driven unsupervised techniques for continuous monitoring of arousal trend of users.

BACKGROUND

Neuroscientific and psychological research suggest that emotion plays an important role in influencing intelligence, rationality, behavior and inter-personal interaction. Emotional or mental well-being of each individual is essential for their efficient work performance and for maintaining a comfortable social or work environment. Over the world, depression, stress and related emotional disorders are having adverse effects on any organization's productivity, thereby incurring significant monetary losses. Mental health monitoring can detect these disorders in time and proper interventions can be provided thereafter.

A vital step of any mental health monitoring process is to identify the emotional state of a person dynamically over time. According to the widely used Circumplex Model of Affect (e.g., refer 'J. A. Russell, "A circumplex model of affect," Journal of Personality and Social Psychology, vol. 39, no. 06, pp. 1161-1178, 1980.'), each emotion can be mapped to a two-dimensional space defined by two axes, valence and arousal. Valence signifies the pleasantness and arousal represents the intensity of a particular emotion. The center point of this space, having neutral valence and medium arousal, caters to the baseline condition. The emotional state of a person moves on this emotion space over the course of time.

The changes in the emotional state are spontaneously reflected in different physiological signals, e.g., cardiovascular activation, skin conductance, skin temperature, etc. Since these signals are driven by the involuntary Autonomic Nervous System, these can be considered as more reliable modes of emotion recognition than audio-visual emotion channels or questionnaire-based surveys.

Several attempts have been made to determine the emotional state or the valence-arousal level of an individual from physiological data. In traditional research, emotion analyses have been formulated as classification problems. On the other hand, few other researches have treated it as a regression problem where they have designed a real-time continuous arousal monitoring algorithm using features derived from physiological signals. Most of the aforementioned techniques have used supervised approaches for analyzing emotions. The primary challenge in using such approaches is that it is very difficult to obtain a sufficiently large physiological database with 'correct' valence-arousal annotations. This is because the idea of what should be considered as 'correct' in the emotional context is highly person-dependent. Moreover, for a particular person the emotional attributes tend to vary with time, situation and physical health and thus making it even more challenging to estimate the emotional state of a person.

SUMMARY

Embodiments of the present disclosure present technological improvements as solutions to one or more of the above-mentioned technical problems recognized by the inventors in conventional systems. For example, in one aspect, there is provided a processor implemented method for continuous monitoring of arousal trend of users using Heart Rate (HR) driven unsupervised techniques. The processor implemented method, comprising: obtaining instantaneous HR from a resampled time series of RR intervals of an ECG signal specific to user, wherein the instantaneous HR is obtained for a plurality of time windows from the resampled time series; computing, for each time window of the plurality of time windows, a measured average heart rate (a measured $\overline{HR}$) from the instantaneous HR specific to the user; inputting, to a Kalman Filter, the measured average HR (the measured $\overline{HR}$) and an initial estimate of an ideal $\overline{HR}$, wherein the Kalman Filter comprises a state space model that is designed based on baseline dynamics of an average heart rate ($\overline{HR}$); for each time window until a last time window of the plurality of time windows, performing: estimating an apriori state based on a last instance of an aposteriori state being initialized, wherein the initialized aposteriori state is based on the initial estimate of the ideal $\overline{HR}$ fed to the Kalman filter; determining, using the apriori state, an observation of the state space model of the Kalman filter; estimating an error based on the observation and the measured average heart rate (the measured $\overline{HR}$), and normalizing the error thereof; performing a comparison of the normalized error with a pre-defined threshold; and continually monitoring an arousal of the user based on the comparison to obtain an arousal trend.

In an embodiment, the method may further comprise determining, for each time window of the plurality of time windows, a measurement noise of the state space model of the Kalman Filter based on a change in the arousal; and estimating a Kalman gain of the Kalman Filter using the measurement noise.

In an embodiment, the method may further comprise updating, for each time window of the plurality of time windows, the aposteriori state using the Kalman gain. In an embodiment, the measurement noise is adjusted to a value based on the arousal detected.

In an embodiment, the resampled time series is obtained by: receiving the ECG signal pertaining to the user, the ECG signal is captured for a pre-defined time interval; detecting a plurality of R peaks from the ECG signal; determining a time series of RR intervals based on a difference between positions of consecutive R peaks from the plurality of R peaks; filtering outliers from the time series of RR intervals to obtain a corrected time series of RR intervals; and resample, at a predefined sampling rate, the corrected time series of RR intervals using a cubic spline interpolation technique.

In another aspect, there is provided a system for continuous monitoring of arousal trend of users using Heart Rate (HR) driven unsupervised techniques. The system comprise a memory storing instructions; one or more communication interfaces; and one or more hardware processors coupled to the memory via the one or more communication interfaces, wherein the one or more hardware processors are configured by the instructions to: obtain instantaneous HR from a resampled time series of RR intervals of an ECG signal specific to user, wherein the instantaneous HR is obtained for a plurality of time windows from the resampled time series; compute, for each time window of the plurality of time windows, a measured average heart rate (a measured $\overline{HR}$) from the instantaneous HR specific to the user; input, to a Kalman Filter, the measured average heart rate (the measured $\overline{HR}$) and an initial estimate of an ideal average heart rate ($\overline{HR}$), wherein the Kalman Filter comprises a state space model that is designed based on baseline dynamics of an average heart rate ($\overline{HR}$); estimate, for each time window until a last time window of the plurality of time windows, an apriori state based on a last instance of an aposteriori state being initialized, wherein the initialized aposteriori state is based on the initial estimate of the ideal average heart rate ($\overline{HR}$) fed to the Kalman filter; determine for each time window until a last time window of the plurality of time windows, using the apriori state, an observation of the state space model of the Kalman filter; estimate, for each time window until a last time window of the plurality of time windows, an error based on the observation and the measured average heart rate (the measured $\overline{HR}$), and normalizing the error thereof; perform, for each time window until a last time window of the plurality of time windows, a comparison of the normalized error with a pre-defined threshold; and continually monitor, for each time window until a last time window of the plurality of time windows, an arousal of the user based on the comparison to obtain an arousal trend.

In an embodiment, the one or more hardware processors are further configured by the instruction to: determine for each time window until a last time window of the plurality of time windows, based on the estimated arousal trend, a measurement noise of the state space model; and estimate a Kalman gain of the Kalman Filter using the measurement noise.

In an embodiment, the one or more hardware processors are further configured by the instruction to: update, for each time window of the plurality of time windows, the aposteriori state using the Kalman gain.

In an embodiment, the measurement noise is adjusted to a value based on the arousal detected.

In an embodiment, the resampled time series is obtained by: receiving the ECG signal pertaining to the user, the ECG signal is captured for a pre-defined time interval; detecting a plurality of R peaks from the ECG signal; determining a time series of RR intervals based on a difference between positions of consecutive R peaks from the plurality of R peaks; filtering outliers from the time series of RR intervals to obtain a corrected time series of RR intervals; and resample, at a predefined sampling rate, the corrected time series of RR intervals using a cubic spline interpolation technique.

In yet another aspect, there is provided one or more non-transitory machine readable information storage mediums comprising one or more instructions which when executed by one or more hardware processors causes for continuous monitoring of arousal trend of users using Heart Rate (HR) driven unsupervised techniques by obtaining instantaneous HR from a resampled time series of RR intervals of an ECG signal specific to user, wherein the instantaneous HR is obtained for a plurality of time windows from the resampled time series; computing, for each time window of the plurality of time windows, a measured average heart rate (a measured $\overline{HR}$) from the instantaneous HR specific to the user; inputting, to a Kalman Filter, the measured average heart rate (the measured $\overline{HR}$) and an initial estimate of an ideal $\overline{HR}$, wherein the Kalman Filter comprises a state space model that is designed based on baseline dynamics of an average heart rate ($\overline{HR}$); for each time window until a last time window of the plurality of time windows, performing: estimating an apriori state based on a last instance of an aposteriori state being initialized, wherein the initialized aposteriori state is based on the initial estimate of the ideal $\overline{HR}$ fed to the Kalman filter; determining, using the apriori state, an observation of the state space model of the Kalman filter; estimating an error based on the observation and the measured average heart rate (the measured $\overline{HR}$), and normalizing the error thereof; performing a comparison of the normalized error with a pre-defined threshold; and continually monitoring an arousal of the user based on the comparison to obtain an arousal trend.

In an embodiment, the instructions which when executed by the one or more hardware processors may further cause determining, for each time window of the plurality of time windows, a measurement noise of the state space model of the Kalman Filter based on a change in the arousal; and estimating a Kalman gain of the Kalman Filter using the measurement noise.

In an embodiment, the instructions which when executed by the one or more hardware processors may further cause updating, for each time window of the plurality of time windows, the aposteriori state using the Kalman gain. In an embodiment, the measurement noise is adjusted to a value based on the arousal detected.

In an embodiment, the resampled time series is obtained by: receiving the ECG signal pertaining to the user, the ECG signal is captured for a pre-defined time interval; detecting a plurality of R peaks from the ECG signal; determining a time series of RR intervals based on a difference between positions of consecutive R peaks from the plurality of R peaks; filtering outliers from the time series of RR intervals to obtain a corrected time series of RR intervals; and resample, at a predefined sampling rate, the corrected time series of RR intervals using a cubic spline interpolation technique.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
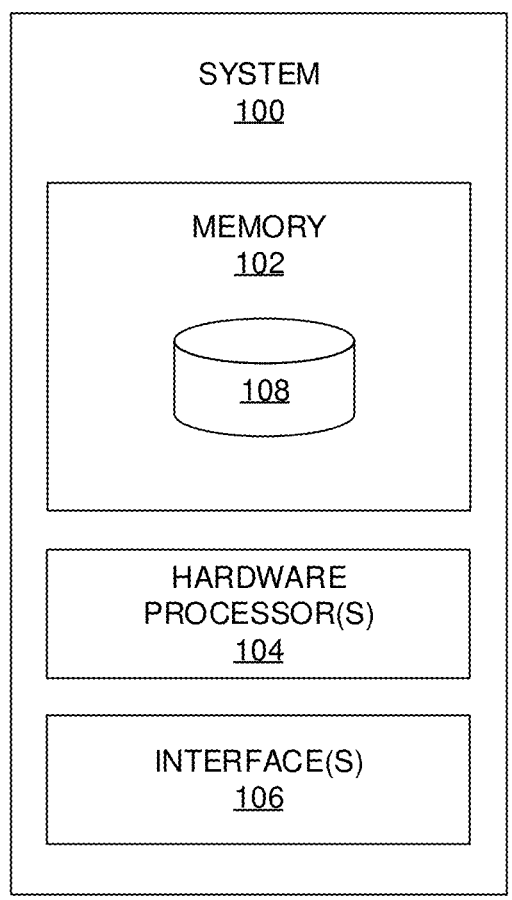
FIG. 1 illustrates an exemplary block diagram of a system for continuous monitoring of arousal trend of users using Heart Rate (HR) driven unsupervised techniques in accordance with an embodiment of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Existing techniques have been classifying broad levels of arousal (low/medium/high or baseline/arousal) but have been insufficient to provide any information about how the arousal level of a person is changing over time. This continuous arousal trend information is essential to have a proper understanding about the dynamics of the affective behavior of the person over time. Further, many of these existing techniques have used supervised approaches for analyzing emotions. The primary challenge in using such approaches is that it is very difficult to obtain a sufficiently large physiological database with 'correct' valence-arousal annotations. This is because the idea of what should be considered as 'correct' in the emotional context is highly person-dependent. Moreover, for a particular person the emotional attributes tend to vary with time, situation and physical health. Though using self-reports as the ground truth annotations seems to be a viable choice but different persons may perceive the same emotion differently. Thus, self-reports tend to be biased and there is no universally accepted method/technique of removing this bias. Considering these difficulties, an unsupervised emotion monitoring system seems to be a more realistic choice.

Under normal condition, heart rate (HR) of a healthy individual varies between 60 and 100 bpm. Any increase in the arousal level leads to an increasing trend in HR. Thus by an accurate study of the temporal variations of the $\overline{HR}$, an overall estimate of the arousal trend can be determined. Though it is very difficult to detect an arbitrary person's absolute level of arousal, the direction of arousal change (i.e., increasing/decreasing/no change) can be identified by the proposed method.

Embodiments of the present disclosure propose a continuous and unsupervised approach of monitoring the arousal trend of an individual from his heart rate using Kalman Filter. State-space model of the Kalman filter characterizes the baseline arousal condition. Deviations from this baseline model are used to recognize the arousal trend. The primary assumption behind the Kalman Filter is that the state $\alpha_t$ should follow a single linear Gaussian distribution. However, the distribution of $\overline{HR}$ (i.e., its mean and standard deviation) changes with any change in the arousal level. Observing this, the state-space model of the Kalman Filter is constructed to capture only the baseline condition of average heart rate ($\overline{HR}$). In the proposed framework, at any time t, the state $\alpha_t$ signifies the ideal $\overline{HR}$ for the baseline condition and the model observation $\beta_t$ denotes the measured average heart rate (the measured $\overline{HR}$). During baseline, $\overline{HR}$ is not expected to vary significantly over consecutive time instants. The state model, given by (1), implements this fact by assuming $\overline{HR}$ to be constant over time with the only perturbation from a zero-mean, white, Gaussian noise called the process noise. This noise models the variations in HR associated with normal sinus rhythm. The measurement model, denoted by (2), relates the ideal $\overline{HR}$ estimated from the state model to the measured average heart rate (or the measured $\overline{HR}$) which again involves a zero-mean, white, Gaussian noise called the measurement noise. The measurement noise represents the errors incurred during measurement.

$$\alpha_t = \alpha_{t-1} + \text{process noise} \quad (1)$$

$$\beta_t = \alpha_t + \text{measurement noise} \quad (2)$$

The deviation of the physically measured average heart rate (the measured $\overline{HR}$) from the baseline value estimated adaptively by the state-space model of the Kalman Filter is used to infer the arousal trend. Since the state model, given by (1), represents the condition of no arousal change, the $\overline{HR}$ values, for which arousal changes are detected, are treated as unreliable measurements. Hence their effect in refining the model estimates are to be reduced. This is done by increasing the variance of the measurement noise when any change in arousal is detected.

The proposed methods and systems were implemented by the present disclosure for validation by using a publicly available dataset, DECAF (DECoding AFfective), comprising the physiological responses of 30 subjects (or users) while watching 'x' number of video clips (36 movie clips) inducing different emotions. For each clip, annotations of arousal given by experts per second are used to quantify the ground truth of arousal change. Experimental results suggest that the proposed method achieves a median correlation of 0.53 between the computed and expected arousal levels which is significantly higher than that achievable by the state-of-the-art technique(s).

Referring now to the drawings, and more particularly to FIGS. 1 through 5H, where similar reference characters denote corresponding features consistently throughout the figures, there are shown preferred embodiments and these embodiments are described in the context of the following exemplary system and/or method.

FIG. 1 illustrates an exemplary block diagram of a system 100 for continuous monitoring of arousal trend of users using Heart Rate (HR) driven unsupervised techniques in accordance with an embodiment of the present disclosure. In an embodiment, the system 100 may also be referred as an Arousal Detection System (ADS), and interchangeably used hereinafter. In an embodiment, the system 100 includes one or more processors 104, communication interface device(s) or input/output (I/O) interface(s) 106, and one or more data storage devices or memory 102 operatively coupled to the one or more processors 104. The memory 102 comprises a database 108. The one or more processors 104 that are hardware processors can be implemented as one or more microprocessors, microcomputers, microcontrollers, digital signal processors, central processing units, state machines, logic circuitries, and/or any devices that manipulate signals based on operational instructions. Among other capabilities, the processor(s) is configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud and the like.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes.

The database 108 may store information but are not limited to, ECG signal (or Electrocardiography signal or Electrocardiogram signal)_and information from the ECG signal pertaining to user(s), and the like. Further, the database 108 stores information pertaining to inputs fed to the system 100 and/or outputs generated by the system (e.g., at each stage), specific to the methodology described herein. More specifically, the database 108 stores information being processed at each step of the proposed methodology.

Figure 2:
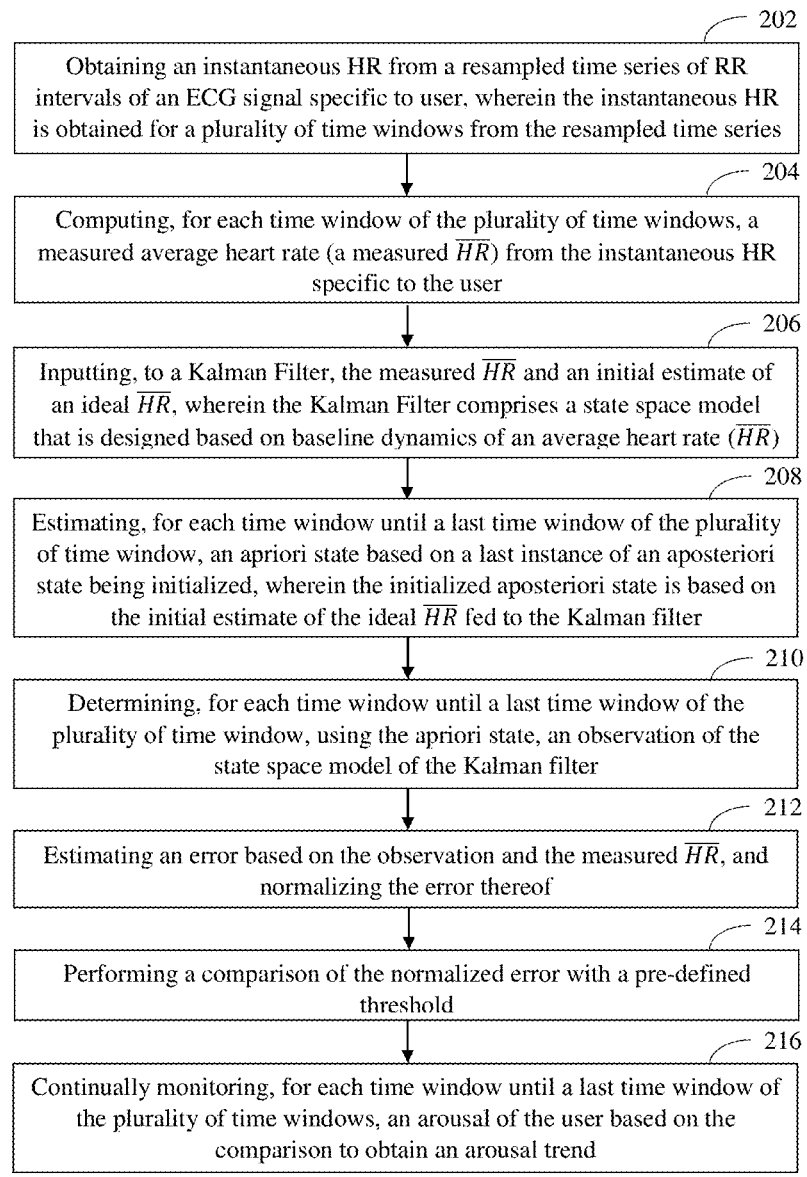
FIG. 2 illustrates an exemplary flow diagram illustrating a method for continuous monitoring of arousal trend of users using Heart Rate (HR) driven unsupervised techniques using the system of FIG. 1 in accordance to an embodiment of the present disclosure.

FIG. 2, with reference to FIG. 1, illustrates an exemplary flow diagram illustrating a method for continuous monitoring of arousal trend of users using Heart Rate (HR) driven unsupervised techniques using the system 100 of FIG. 1 according to an embodiment of the present disclosure. In an embodiment, the system 100 comprises one or more data storage devices or the memory 102 operatively coupled to the one or more hardware processors 104 and is configured to store instructions for execution of steps of the method by the one or more processors 104. The steps of the method of the present disclosure will now be explained with reference to the components of the system 100 as depicted in FIG. 1, and the flow diagram of FIG. 2. In an embodiment of the present disclosure, at step 202, the one or more hardware processors 104 obtain instantaneous HR from a resampled time series of RR intervals of an ECG signal specific to user. In an embodiment, the resampled time series is obtained by: receiving the ECG signal pertaining to the user, the ECG signal is captured for a pre-defined time interval; detecting a plurality of R peaks from the ECG signal; and determining a time series of RR intervals based on 2 consecutive R peaks. The time series of RR intervals is determined by using a difference between positions of 2 consecutive R peaks from the plurality of peaks detected, in one example embodiment. In an embodiment, the R peak(s) are identified using modified Pan Tompkin's algorithm/technique. Further, outliers from the time series of RR intervals are filtered to obtain a corrected time series of RR intervals and the corrected time series of RR intervals is resampled using a cubic spline interpolation technique. Assuming that mean and standard deviation of the obtained RR intervals are $\mu_{RR}$ and $\sigma_{RR}$ respectively. Samples of the time series lying outside a range (e.g., say $\mu_{RR} \pm 2\sigma_{RR}$) may be treated as outliers and, hence, discarded and the remaining samples are resampled (e.g., using the cubic spline interpolation) at a uniform sampling frequency of say 1 Hertz to obtain a resampled time series. Inverse of the RR intervals in the resampled time series gives the instantaneous HR.

In an embodiment of the present disclosure, at step 204 the one or more hardware processors 104 compute a measured average heart rate ($\overline{HR}$) from the instantaneous HR specific to the user, and the measured average heart rate (the measured $\overline{HR}$) is inputted along with an initial estimate of an ideal $\overline{HR}$ to a Kalman Filter (KF) (not shown in FIG. 1) at step 206. In an embodiment of the present disclosure, the expression "average heart rate" is denoted by ($\overline{HR}$). Therefore measured average heart rate may also be referred as 'measured $\overline{HR}$', in one example embodiment of the present disclosure, and may be interchangeably used hereinafter. In an embodiment of the present disclosure, the measured $\overline{HR}$ is computed for each time window until a last time window from the plurality of time windows. The Kalman Filter comprises a state space model, wherein the state space model is designed based on baseline dynamics of an average heart rate ($\overline{HR}$), in an example embodiment. In an embodiment of the present disclosure, the measure average heart rate (the measured $\overline{HR}$) is computed by averaging instantaneous HR values over a period of time windows with a certain percentage of overlap. In the present disclosure, the systems and methods of the present disclosure has computed the measured $\overline{HR}$ by averaging instantaneous HR values over 10 seconds time windows with a 90% overlap. This window-wise averaging operation performs smoothing over the normal heart rate variability and thereby the measured averaged heart rate (the measured $\overline{HR}$) provides the slow-varying HR trend.

In an embodiment of the present disclosure, the Kalman Filter is comprised in the memory 102 and executed to perform the steps of the present disclosure and methodology described herein.

The primary assumption behind the KF is that the state $\alpha_t$ should follow a single linear Gaussian distribution. However, the distribution of $\overline{HR}$ (i.e., its mean and standard deviation) changes with any change in the arousal level. Keeping this in mind, the state-space model of the KF is constructed to capture only the baseline $\overline{HR}$ condition. The deviation of the physically measured $\overline{HR}$ from the baseline value estimated adaptively by the KF is then used to infer the arousal trend as described below herein.

In an embodiment of the present disclosure, at step 208 the one or more hardware processors 104 estimate an apriori state based on a last instance of an initialized aposteriori state, wherein the initialized aposteriori state is based on the initial estimate of the ideal $\overline{HR}$ fed to the Kalman filter. The apriori state is estimated for each time window until the last time window of the plurality of time windows.

In an embodiment of the present disclosure, at step 208 the one or more hardware processors 104 determine, using the apriori state, an observation of the state space model of the Kalman Filter and an error is computed based on the observation and the measured average heart rate (or the measured $\overline{HR}$), and the error is normalized thereof at step 210 to obtain a normalized error. In other words, the error is computed and normalized at each time window from the plurality of time windows.

In an embodiment of the present disclosure, at step 212 the one or more hardware processors 104 perform a comparison of the normalized error with a pre-defined threshold at step 214 and determine an arousal trend of the user based on the comparison at step 216.

In an embodiment of the present disclosure, a measurement noise of the state space model of the Kalman Filter is determined for each time window of the plurality of time windows based on a change in the arousal and a Kalman gain of the Kalman Filter is estimated using the measurement noise respectively. Based on the Kalman gain, the system 100 or the hardware processors 104 further update, for each time window of the plurality of time windows, the aposteriori state. In an embodiment, the measurement noise is adjusted to a value based on the arousal detected. Once the aposteriori state is updated the steps 208 till 216 are repeated for detecting arousal of user and obtaining arousal trend thereof. In other words, during the repetition of steps 208 till 216, each time the measurement noise is determined for computing Kalman gain at each time window and the aposterior state updation happens accordingly.

In the present disclosure, at any time t, the state $\alpha_t$ signifies the ideal $\overline{HR}$ for the baseline condition and observation state $\beta_t$ denotes the measured $\overline{HR}$. During baseline, $\overline{HR}$ is not expected to vary significantly over consecutive time instants. The state model, given by equation (1), implements this fact by assuming $\overline{HR}$ to be constant over time with the only perturbation from a zero-mean, white, Gaussian noise $\omega_t$ (process noise) of variance $Y_t$. Here $\omega_t$ models the $\overline{HR}$ variations associated with normal sinus rhythm. The measurement model, denoted by equation (2), relates the ideal $\overline{HR}$ estimated from the state space model to the measured $\overline{HR}$ which again involves a zero-mean, white, Gaussian noise $v_t$ (measurement noise) representing error(s) incurred during measurement. The variance of $v_t$ is represented by $\Gamma_t$.

$$\alpha_t = \alpha_{t-1} + \omega_t, \text{where}, \omega_t \sim \mathcal{N}(0, Y_t) \quad (1)$$

$$\beta_t = \alpha_t + v_t, \text{where}, v_t \sim \mathcal{N}(0, \Gamma_t) \quad (2)$$

where $\mathcal{N}(m, s^2)$ denotes a Gaussian distribution with mean m and variance $s^2$ At each time instant t, the following steps are performed to detect the arousal trend of the subject.

The steps 208 till 216 and measurement noise, Kalman gain and updation/correction of the aposteriori state are described by of example below.

Prediction: As described in step 108, first, the apriori state at and corresponding variance $\Lambda_t^-$ are computed as below:

$$\alpha_t^- = \alpha_{t-1}^+ \quad (3)$$

$$\Lambda_t^- = \Lambda_{t-1}^+ + Y_t \quad (4)$$

where $\alpha_{t-1}^+$ and $\Lambda_{t-1}^+$ denote the aposteriori state and variance at time t−1 respectively. Since normal $\overline{HR}$ lies in [60, 100] bpm, the initial state estimate, $\alpha_0^-$, is set to the average of this range, i.e., 80 bpm. The variance estimate is initialized to a value (e.g., say small value) given by $\Lambda_0^+ = 0.01$. The observation state $\beta_t$ is then obtained as follows:

$$\beta_t = \alpha_t^- \quad (5)$$

Error estimation: The error $\Delta_t$ between the $\overline{HR}$ trend $\overline{HR}_t$ obtained from ECG at time t and the observation $\beta_t$ estimated by the Kalman Filter is obtained by equation (6). The present disclosure introduces equation (7) in order to model the normalized error, $\widetilde{\Delta}_t$, where $\mu_t$ and $\sigma_t$ denote the mean and standard deviation of $\Delta_i$ for i=1, . . . (t−1).

$$\Delta_t = \overline{HR}_t - \beta_t \quad (6)$$

$$\widetilde{\Delta}_t = \frac{\Delta_t - \mu_t}{\sigma_t} \quad (7)$$

It is to be noted that, as the state estimate is initialized to 80 bpm and the averaging of instantaneous $\overline{HR}$ over overlapping windows is done for the measurement only, the Markov assumption of KF is not violated.

Arousal detection: With an increase (or decrease) in arousal, $\overline{HR}_t$ is assumed to rise (or fall) significantly, which in turn, changes $\Delta_t$ accordingly. Thus if $\Delta_t$ is sufficiently higher (or lower) than the error trend till that instant, i.e., $\widetilde{\Delta}_t$ assumes a significant positive (or negative) value, an increase (or decrease) in arousal level as compared to that of previous instant is inferred. If absolute value of $\Delta_t$ remains within a threshold $\lambda$ then it is decided that the arousal level has not changed. The present disclosure propose to quantify the direction of arousal change as $\xi_t$ in equation (8). Here the values 0, 1 and −1 of $\xi_t$ represent no change, an increase and a decrease in arousal level respectively.

$$\xi_t = \begin{cases} 0, |\widetilde{\Delta}_t| \leq \lambda \\ 1, \widetilde{\Delta}_t > \lambda \\ -1, \widetilde{\Delta}_t < -\lambda \end{cases} \quad (8)$$

Thus, the arousal level $A_t$ at time t is defined as, $$A_t = A_{t-1} + \xi_t \quad (9)$$

Here it is noteworthy that the estimated numerical value of $A_t$ does not carry much significance, rather the pattern or trend of the $A_t$ time-series is important.

Updation/Correction: Since the state space model, given by (1), represents the condition of no arousal change, the $\overline{HR}_t$ values, for which an arousal change is detected, are treated as unreliable measurements. Hence their effect in refining the model estimates are to be reduced. This is done by increasing the variance $\Gamma_t$ of the measurement noise as follows:

$$\Gamma_t = (1 - |\xi_t|)\psi_t + |\xi_t|P\psi_t \quad (10)$$

Here, $\psi_t$ denotes an estimate of the variance of measurement noise during baseline condition and P is a positive multiplier that helps in increasing $\Gamma_t$ when $\xi_t$ is ±1.

Now the Kalman gain $G_t$ is determined by equation (11). Finally the refined (or updated/corrected) aposteriori state $\alpha_t^+$ and corresponding variance $\Lambda_t^+$ are obtained by equation (12) and (13), respectively, as shown below by way of example expressions:

$$G_t = \frac{\Lambda_t^-}{\Lambda_t^- + \Gamma_t} \quad (11)$$

$$\alpha_t^+ = \alpha_t^- + G_t \Delta_t \quad (12)$$

$$\Lambda_t^+ = (1 - G_t)\Lambda_t^- \quad (13)$$

The process noise variance $Y_t$ models the small changes in the ideally constant baseline $\overline{HR}$ due to sinus rhythm. Whereas, $\psi_t$ involves relatively larger variations in the physically measured baseline $\overline{HR}$ due to other physiological and instrumental perturbations. Hence, $Y_t$ should be considerably smaller than $\psi_t$. Here the system 100 heuristically choose $Y_t=0.001$ and $\psi_t=0.01$. Further, on detection of any arousal change, the measurement noise variance is increased ($\Lambda_t$, as shown in equation (10)) significantly. Hence, the multiplier P is set to a high value of 10. Finally, threshold $\lambda$ is experimentally set as 0.5.

Dataset:

The proposed methodology was validated on the movie portion of a publicly available dataset DECAF—a multimodal database for DECoding AFfective user responses (e.g., refer 'M. K. Abadi, R. Subramanian, S. M. Kia, P. Avesani, I. Patras, and N. Sebe, "DECAF: MEG-based multimodal database for decoding affective physiological responses," IEEE Transactions on Affective Computing, vol. 6, no. 3, pp. 209-222, 2015.'). It contains the affective responses of 30 subjects (16 male) aged 27.3±4.3 years. Each subject watched 36 movie clips spread across nine different emotional genres including happy, sad, exciting, angry etc. The duration of a clip was 79.97±20.37 seconds. The clips were shown in two sessions each comprising 18 videos. A random order was maintained in each session such that two videos of similar emotional characteristics were not shown successively. During these sessions, ECG (along with other physiological signals) of the subjects were recorded at a sampling frequency of 1 kHz. Seven expert annotators provided per-second arousal ratings ranging between [−1, 1] for each movie clip. The median of the seven annotations at each time instant is taken as the ground truth (GT) for all analysis as suggested by dataset creators (e.g., refer 'M. K. Abadi, R. Subramanian, S. M. Kia, P. Avesani, I. Patras, and N. Sebe, "DECAF: MEG-based multimodal database for decoding affective physiological responses," IEEE Transactions on Affective Computing, vol. 6, no. 3, pp. 209-222, 2015.').

Results and Discussion:

Results were obtained by applying the proposed KF based arousal trend monitoring technique on DECAF movie dataset and a thorough discussion on the advantages of this technique are discussed. It is shown that the predicted arousal time-series A can be used as a direct measure of arousal, compared to the traditional $\overline{HR}$ time-series. The proposed is also compared with the supervised regressive approach given in traditional research (e.g., refer 'B. Grundlehner, L. Brown, J. Penders, and B. Gyselinckx, "The design and analysis of a real-time, continuous arousal monitor," in Wearable and Implantable Body Sensor Networks, BSN. Sixth International Workshop on. IEEE, 2009, pp. 156-161.'). The efficacy of these candidate arousal measures are compared based on the following performance metrics.

1. Pearson's correlation coefficient ($\rho$) with GT.
2. Minimum Euclidean distance ($\delta$) from GT computed by Dynamic Time Warping (DTW).

While computing $\delta$, the two candidate time-series (measure of arousal and GT) are mapped to [0, 1]. The obtained metric was divided by the length of the aligned time-series in order to bring all the $\delta$ values on the same ground for comparison. High value of $\rho$ and low value of $\delta$ indicate good trend monitoring performance.

Figure 3A:
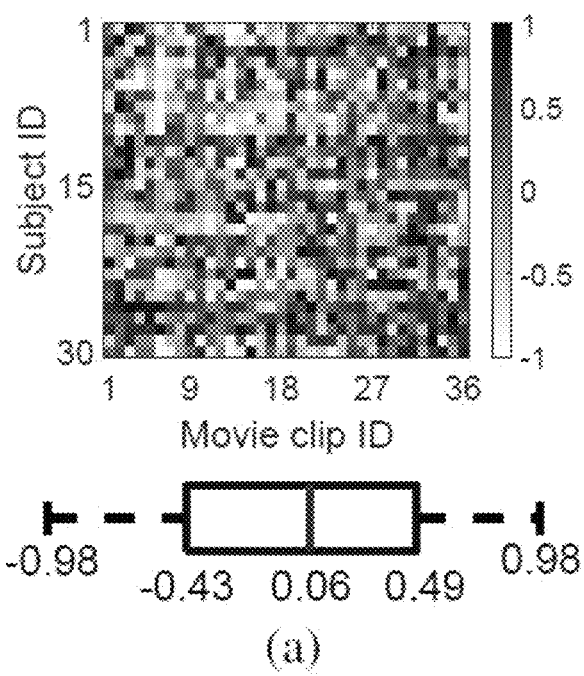
FIGS. 3A-3B depict correlation analysis of ground truth arousal annotation with (a) $\overline{HR}$, (b) arousal time-series A obtained using Kalman Filter (KF) approach implemented by the system of FIG. 1 in accordance with an example embodiment of the present disclosure.
Figure 3B:
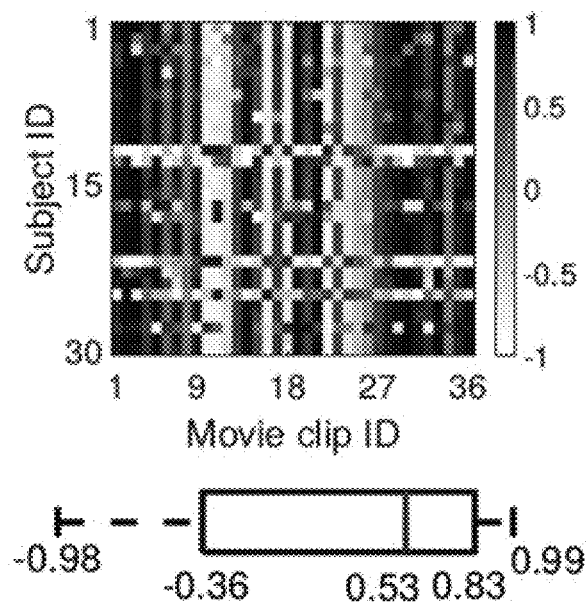

$\overline{HR}$ versus A—performance as an arousal measure:

As mentioned in the above description, a rise in the HR trend corresponds to an increasing arousal level. The formulation of the proposed technique also incorporates this supposition. In order to examine the benefit of the KF based arousal monitoring approach, the present disclosure first considers using the $\overline{HR}$ directly as a measure of arousal. FIG. 3A shows that though a relation between $\overline{HR}$ and arousal is reported, there is no significant correlation (low median and high interquartile range) present in the current case; whereas, in case of A obtained by the KF, as shown in FIG. 3B, the correlation measures are significantly better with an increase of 0.47 in the median value. Moreover, the values of $\rho$ for $\overline{HR}$ spans evenly over the entire range, whereas, in case of the arousal measure A the $\rho$ values are mainly concentrated in the high correlation region. The second performance metric $\delta$ reported in FIG. 4A-4B, also reflects the superiority of A over $\overline{HR}$ as a measure of arousal.

Figure 4A:
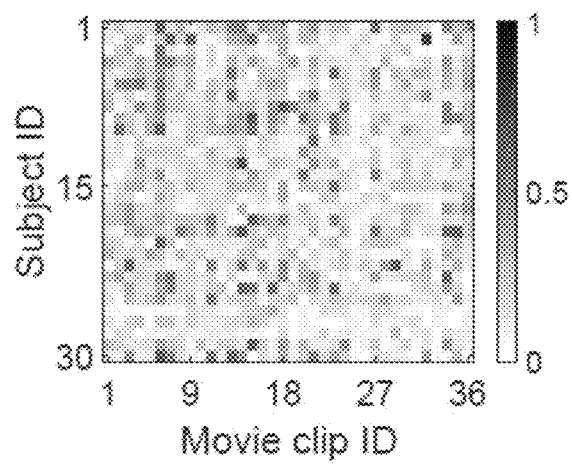
FIGS. 4A-4B depict Dynamic Time Warping (DTW) analysis of ground truth arousal annotation with (a) $\overline{HR}$, (b) arousal time-series A obtained using the KF approach implemented by the system of FIG. 1 in accordance with an example embodiment of the present disclosure.
Figure 4B:
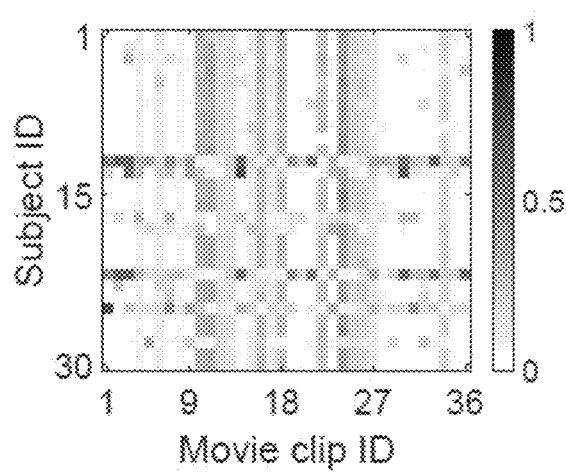

More specifically, FIGS. 3A-3B, with reference to FIGS. 1 through 2, depict correlation analysis of ground truth arousal annotation with (a) $\overline{HR}$, (b) arousal time-series A obtained using KF approach in accordance with an example embodiment of the present disclosure. FIGS. 4A-4B, with reference to FIGS. 1 through 3B, depict Dynamic Time Warping (DTW) analysis of ground truth arousal annotation with (a) $\overline{HR}$, (b) arousal time-series A obtained using KF approach in accordance with an example embodiment of the present disclosure.

Moreover, both FIGS. 3A through 4B show that there exists a pattern in the values of the performance metrics obtained in case of A unlike that for $\overline{HR}$, i.e., the KF model consistently performs well for the majority of movie clips, whereas the performance of $\overline{HR}$ is completely random. This substantiates the feasibility of the proposed model. The reason behind the not good performance of $\overline{HR}$, in spite of its reported relation with arousal, might be the presence of noise in the ECG signal from which $\overline{HR}$ is derived. This noise is reduced using the KF, thereby making A a more robust measure of arousal. Moreover the KF takes into account the slow variations of the baseline $\overline{HR}$ over time, which again facilitates obtaining a better estimate of arousal.

Figure 5A:
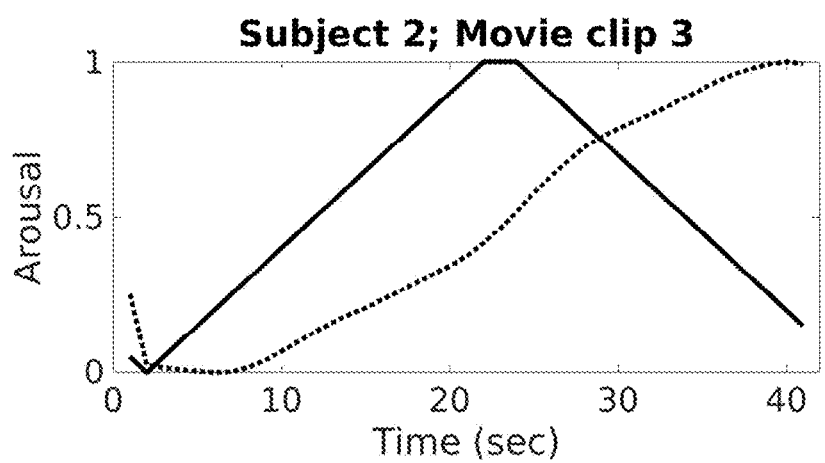
FIGS. 5A through 5H depict graphical representations illustrating ground truth annotations and corresponding arousal level time-series obtained using the KF approach implemented by the system of FIG. 1 in accordance with an example embodiment of the present disclosure.
Figure 5B:
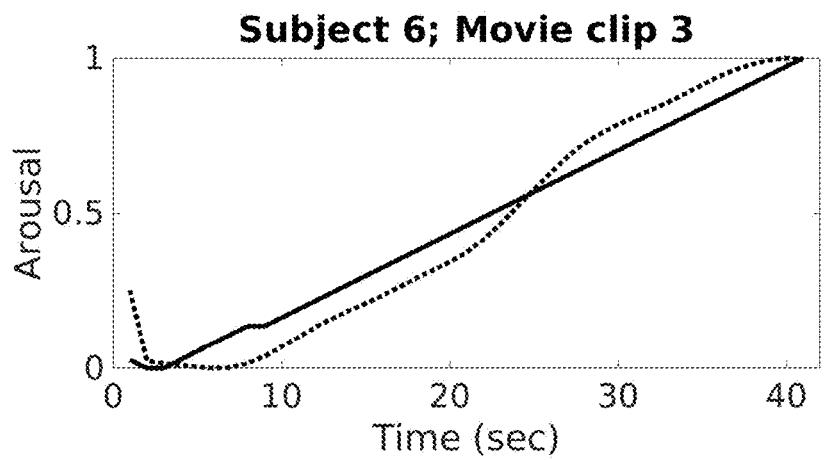
Figure 5C:
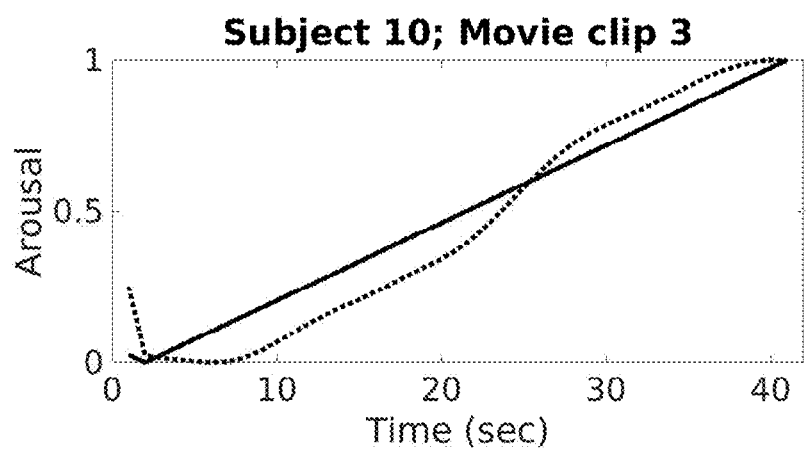
Figure 5D:
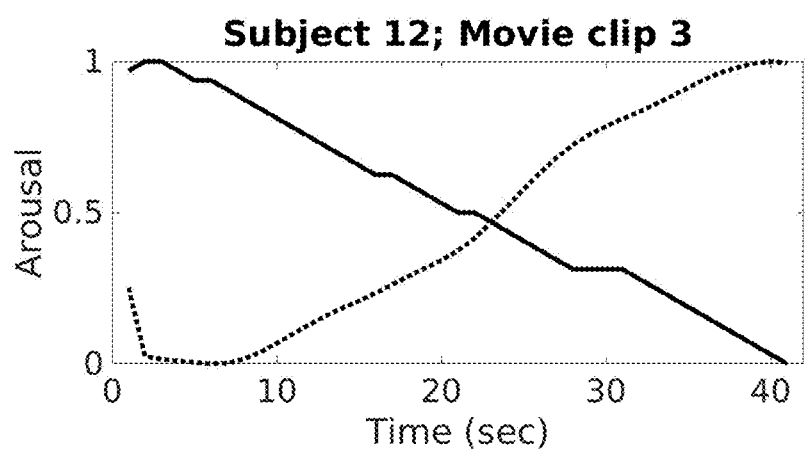
Figure 5E:
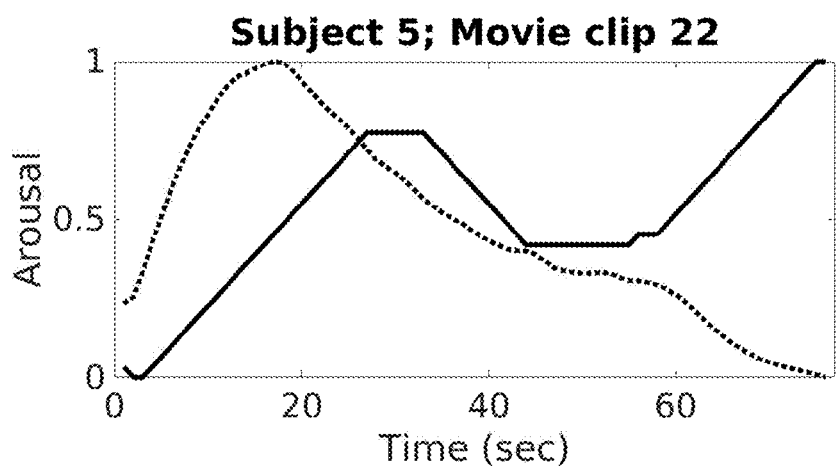
Figure 5F:
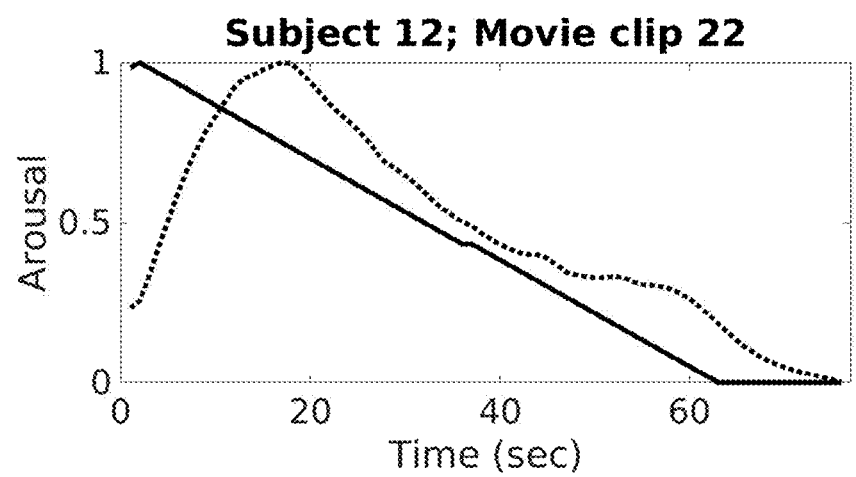
Figure 5G:
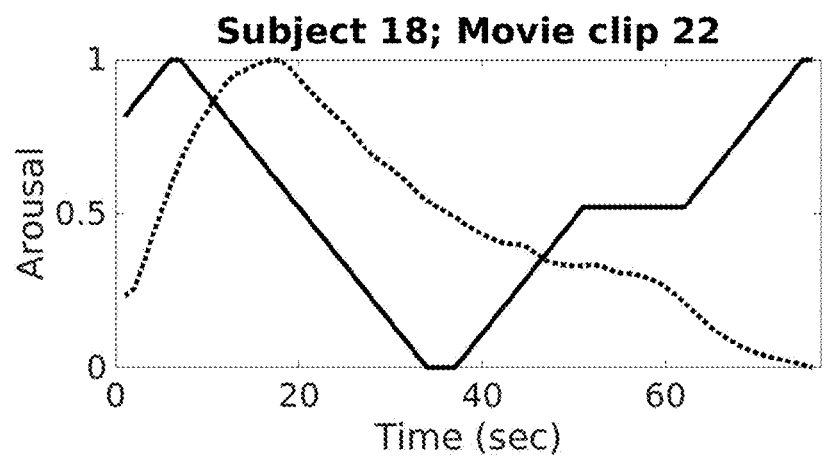
Figure 5H:
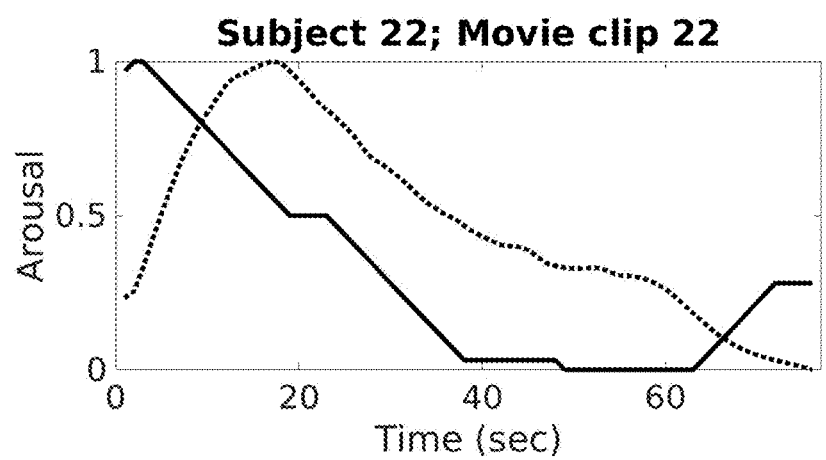

Analysis of Trend Predictions:

FIGS. 5A through 5H, with reference to FIGS. 1 through 4B, depict graphical representations illustrating ground truth annotations and corresponding arousal level time-series obtained using the KF approach in accordance with an example embodiment of the present disclosure. More specifically, FIGS. 5A through 5H present representative cases of the DECAF dataset. In the graphical representations depicted in FIGS. 5A through 5H, dotted line representation indicates ground truth annotations and solid line representation indicates corresponding arousal level time-series, in one example embodiment. Here the arousal time-series A obtained by the proposed KF approach and the corresponding GT are plotted, after mapping both the series to the range [0, 1]. It can be seen that the trend of A resembles that of GT significantly in most of the cases, whereas, the resemblance is less prominent in some others. Even in some cases, as shown in FIG. 5($d$), the KF may not perform as required where it predicts an opposite trend with respect to the GT. An in-depth analysis is performed to study the performance of the proposed technique as below:

Segment-Wise Arousal Analysis:

It is observed that in the cases shown in FIGS. 5A, 5E and 5G, the arousal time-series, A, obtained using the KF approach matches with the GT more during the first half of the movie clip than the last half. In case of FIG. 5F, the resemblance is more during the last half of the clip. Finally, for FIGS. 5B and 5C, the entire sequence is at par with the annotated GT. Table 1 reports the performance metrics $\rho$ and $\delta$ for both A and $\overline{HR}$ considering different segments of the movie clips. More specifically, Table 1 depicts performance analysis for different video segments.

TABLE 1

| Segment of | $\overline{HR}$ versus GT | | A versus GT | |
|---|---|---|---|---|
| video clip | $\rho$ | $\delta$ | $\rho$ | $\delta$ |
| First half | −0.11 | 0.17 | 0.38 | 0.10 |
| | [−0.66 0.51] | [0.08 0.31] | [−0.41 0.88] | [0.03 0.21] |
| Second half | 0.12 | 0.14 | 0.50 | 0.06 |
| | [−0.51 0.63] | [0.08 0.25] | [−0.45 0.89] | [0.02 0.24] |
| Total | 0.06 | 0.14 | 0.53 | 0.08 |
| | [−0.43 0.49] | [0.09 0.23] | [−0.36 0.83] | ][0.02 0.19] |

It is found that the later segments of the clips have slightly better values of the metrics. This is expected since the $\overline{HR}$ trend in the ECG may not instantaneously reflect the feeling a clip tends to induce.

Table 2 depicts a comparison of the proposed algorithm with traditional systems and methods:

TABLE 2

| Framework | ρ | δ |
|---|---|---|
| Traditional systems and methods | 0.06 [−0.24 0.35] | 0.22 [0.13 0.30] |
| Proposed systems and methods (Kalman Filter) | 0.53 [−0.36 0.83] | 0.08 [0.02 0.19] |

The embodiments of the present disclosure provide systems and methods for continuous arousal trend monitoring that employs the KF technique. Experimental validation on the DECAF movie dataset establishes the efficiency of the proposed method. Compared to $\overline{HR}$, the measure of arousal trend obtained using this proposed technique is found to relate more closely to the GT. This method outperforms the state-of-the-art technique with an increase of 0.47 in the median correlation between the computed and expected arousal levels. It is also observed that the computed arousal trend matches with the GT more during the second half, than the first, of the clips.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor implemented method (200), comprising:
obtaining instantaneous HR from a resampled time series of RR intervals of an ECG signal specific to user, wherein the instantaneous HR is obtained for a plurality of time windows from the resampled time series (202);
computing, for each time window of the plurality of time windows, a measured average heart rate (a measured $\overline{HR}$) from the instantaneous HR specific to the user (204);
inputting, to a Kalman Filter, the measured average heart rate (the measured $\overline{HR}$) and an initial estimate of an ideal $\overline{HR}$, wherein the Kalman Filter comprises a state space model that is designed based on baseline dynamics of an average heart rate ($\overline{HR}$) (206);
for each time window until a last time window of the plurality of time windows, performing:
estimating an apriori state based on a last instance of an aposteriori state being initialized, wherein the initialized aposteriori state is based on the initial estimate of the ideal $\overline{HR}$ fed to the Kalman filter (208);

determining, using the apriori state, an observation of the state space model of the Kalman filter (210);
estimating an error based on the observation and the measured average heart rate (the measured $\overline{HR}$), and normalizing the error thereof (212);
performing a comparison of the normalized error with a pre-defined threshold (214); and
continually monitoring an arousal of the user based on the comparison to obtain an arousal trend (216).

2. The processor implemented method of claim 1, further comprising
determining, for each time window of the plurality of time windows, a measurement noise of the state space model of the Kalman Filter based on a change in the arousal; and
estimating a Kalman gain of the Kalman Filter using the measurement noise.

3. The processor implemented method of claim 2, further comprising updating, for each time window of the plurality of time windows, the aposteriori state using the Kalman gain.

4. The processor implemented method of claim 3, wherein the measurement noise is adjusted to a value based on the arousal detected.

5. The processor implemented method of claim 1, wherein the resampled time series is obtained by:
receiving the ECG signal pertaining to the user, the ECG signal is captured for a pre-defined time interval;
detecting a plurality of R peaks from the ECG signal;
determining a time series of the RR intervals based on a difference between the positions of consecutive R peaks from the plurality of R peaks;
filtering outliers from the time series of the RR intervals to obtain a corrected time series of RR intervals; and
resampling, at a predefined sampling rate, the corrected time series of RR intervals using a cubic spline interpolation technique.

6. A system (100), comprising:
a memory (102) storing instructions;
one or more communication interfaces (106); and
one or more hardware processors (104) coupled to the memory (102) via the one or more communication interfaces (106), wherein the one or more hardware processors (104) are configured by the instructions to:
obtain instantaneous HR from a plurality of time windows within a resampled time series of RR intervals of an ECG signal specific to a user;
compute, for each time window of the plurality of time windows, a measured average heart rate (a measured $\overline{HR}$) from the instantaneous HR specific to the user;
input, to a Kalman Filter, the measured HR and an initial estimate of an ideal $\overline{HR}$, wherein the Kalman Filter comprises a state space model that is designed based on baseline dynamics of an average heart rate ($\overline{HR}$);
for each time window until a last time window of the plurality of time windows:
estimate an apriori state for each time window, based on an initialized aposteriori state, wherein the apriori state is estimated based on a last instance of the initialized aposteriori state, and wherein the initialized aposteriori state is determined based on the initial estimate of the ideal $\overline{HR}$ fed to the Kalman filter;
determine, using the apriori state, an observation of the state space model of the Kalman filter;
estimate, an error based on the observation and the measured $\overline{HR}$, and normalizing the error thereof;
perform, a comparison of the normalized error with a pre-defined threshold; and
obtain an arousal trend of the user by continually monitoring an arousal of the user based on the comparison of the normalized error with the pre-defined threshold.

7. The system of claim 6, wherein the one or more hardware processors are further configured by the instruction to:
determine for each time window until a last time window of the plurality of time windows, based on the estimated arousal trend, a measurement noise of the state space model; and
estimate a Kalman gain of the Kalman Filter using the measurement noise.

8. The system of claim 7, wherein the one or more hardware processors are further configured by the instruction to: update, for each time window of the plurality of time windows, the aposteriori state using the Kalman gain.

9. The system of claim 6, wherein the measurement noise is adjusted to a value based on the arousal detected.

10. The system of claim 6, wherein the resampled time series is obtained by:
receiving the ECG signal pertaining to the user, the ECG signal is captured for a pre-defined time interval;
detecting a plurality of R peaks from the ECG signal;
determining a time series of the RR intervals based on a difference between positions of consecutive R peaks from the plurality of R peaks detected;
filtering outliers from the time series of the RR intervals to obtain a corrected time series of RR intervals; and
resampling, at a predefined sampling rate, the corrected time series of RR intervals using a cubic spline interpolation technique.

11. One or more non-transitory machine readable information storage mediums comprising one or more instructions which when executed by one or more hardware processors cause:
obtaining instantaneous HR from a resampled time series of RR intervals of an ECG signal specific to user, wherein the instantaneous HR is obtained for a plurality of time windows from the resampled time series;
computing, for each time window of the plurality of time windows, a measured average heart rate (a measured $\overline{HR}$) from the instantaneous HR specific to the user;
inputting, to a Kalman Filter, the measured average heart rate (the measured $\overline{HR}$) and an initial estimate of an ideal HR, wherein the Kalman Filter comprises a state space model that is designed based on baseline dynamics of an average heart rate ($\overline{HR}$);
for each time window until a last time window of the plurality of time windows, performing:
estimating an apriori state based on a last instance of an aposteriori state being initialized, wherein the initialized aposteriori state is based on the initial estimate of the ideal $\overline{HR}$ fed to the Kalman filter;
determining, using the apriori state, an observation of the state space model of the Kalman filter;
estimating an error based on the observation and the measured average heart rate (the measured $\overline{HR}$), and normalizing the error thereof;
performing a comparison of the normalized error with a pre-defined threshold; and
continually monitoring an arousal of the user based on the comparison to obtain an arousal trend.

12. The one or more non-transitory machine readable information storage mediums of claim 11, wherein the instructions further cause:
- determining, for each time window of the plurality of time windows, a measurement noise of the state space model of the Kalman Filter based on a change in the arousal; and
- estimating a Kalman gain of the Kalman Filter using the measurement noise.

13. The one or more non-transitory machine readable information storage mediums of claim 12, wherein the instructions further cause updating, for each time window of the plurality of time windows, the aposteriori state using the Kalman gain.

14. The one or more non-transitory machine readable information storage mediums of claim 13, wherein the measurement noise is adjusted to a value based on the arousal detected.

15. The one or more non-transitory machine readable information storage mediums of claim 11, wherein the resampled time series is obtained by:
- receiving the ECG signal pertaining to the user, the ECG signal is captured for a pre-defined time interval;
- detecting a plurality of R peaks from the ECG signal;
- determining a time series of the RR intervals based on a difference between the positions of consecutive R peaks from the plurality of R peaks;
- filtering outliers from the time series of the RR intervals to obtain a corrected time series of RR intervals; and
- resampling, at a predefined sampling rate, the corrected time series of RR intervals using a cubic spline interpolation technique.

* * * * *